(12) United States Patent
Cicero et al.

(10) Patent No.: US 11,737,704 B2
(45) Date of Patent: Aug. 29, 2023

(54) SYSTEMS AND METHODS FOR APPROXIMATING BONE MINERAL DENSITY AND FRACTURE RISK USING SINGLE ENERGY X-RAYS

(71) Applicant: 16 Bit Inc., Toronto (CA)

(72) Inventors: Mark Cicero, Ancaster (CA); Alexander Bilbily, Toronto (CA); Daniel Eftekhari, Toronto (CA)

(73) Assignee: 16 BIT INC., Ontario (CA)

( * ) Notice: Subject to any disclaimer, the term of this patent is extended or adjusted under 35 U.S.C. 154(b) by 449 days.

(21) Appl. No.: 16/931,050

(22) Filed: Jul. 16, 2020

(65) Prior Publication Data
US 2021/0015421 A1 Jan. 21, 2021

Related U.S. Application Data

(60) Provisional application No. 62/874,502, filed on Jul. 16, 2019.

(51) Int. Cl.
*G06K 9/00* (2022.01)
*A61B 5/00* (2006.01)
(Continued)

(52) U.S. Cl.
CPC .......... *A61B 5/4509* (2013.01); *A61B 5/7267* (2013.01); *A61B 5/7275* (2013.01);
(Continued)

(58) Field of Classification Search
None
See application file for complete search history.

(56) References Cited

U.S. PATENT DOCUMENTS

| | | | | |
|---|---|---|---|---|
| 6,654,445 B2 * | 11/2003 | Shepherd | ............... | A61B 6/508 378/53 |
| 2003/0142780 A1 * | 7/2003 | Shepherd | ............. | G01N 23/083 378/37 |

(Continued)

FOREIGN PATENT DOCUMENTS

WO WO 2016/013004 A1 1/2016

OTHER PUBLICATIONS

Adams, J. E. "Single-and dual-energy: X-ray absorptiometry." Bone densitometry and osteoporosis (1998): 305-334. (Year: 1998).*

(Continued)

*Primary Examiner* — Avinash Yentrapati
(74) *Attorney, Agent, or Firm* — FENWICK & WEST LLP

(57) ABSTRACT

A computerized method for estimating bone mineral density, z and t-scores and/or fracture risk by receiving single-energy x-rays of the thoracic spine, chest x-ray, lumbar spine, whole body x-ray, hip, arm, leg, hand or foot in addition to imaging technical parameters and clinical parameters such as patient demographics, medical history, and other risk factors. The results are presented to a user for the diagnosis or screening of osteoporosis and/or risk stratification of osteoporotic fractures. A classifier may be trained using a dataset of single energy x-rays correlated to results from dual energy x-ray readings performed in the same patient and of the same body part, along with fracture incidence, to correlate the inputs provided to the desired output. A classifier may also be trained to predict fracture risk directly from x-ray image data and optionally additional patient characteristics.

16 Claims, 4 Drawing Sheets

(51) Int. Cl.
  *G16H 30/20* (2018.01)
  *G16H 50/30* (2018.01)
  *G16H 10/60* (2018.01)
  *G16H 30/40* (2018.01)
  *G06N 3/047* (2023.01)

(52) U.S. Cl.
  CPC ............. *G06N 3/047* (2023.01); *G16H 10/60* (2018.01); *G16H 30/20* (2018.01); *G16H 30/40* (2018.01); *G16H 50/30* (2018.01)

(56) References Cited

U.S. PATENT DOCUMENTS

| | | | | |
|---|---|---|---|---|
| 2003/0194120 | A1* | 10/2003 | Unger | A61B 6/405 382/132 |
| 2006/0222228 | A1* | 10/2006 | Hobert | G06T 7/0012 382/132 |
| 2007/0047794 | A1* | 3/2007 | Lang | A61B 6/583 382/132 |
| 2007/0058786 | A1* | 3/2007 | Michael | A61B 6/583 378/207 |
| 2007/0223799 | A1* | 9/2007 | Weiss | G16H 70/60 382/131 |
| 2010/0310141 | A1* | 12/2010 | Wilson | A61B 6/482 600/300 |
| 2011/0257507 | A1* | 10/2011 | Gregory | A61B 6/505 600/407 |
| 2012/0029355 | A1* | 2/2012 | Marom | A61B 8/4488 600/459 |
| 2016/0015347 | A1* | 1/2016 | Bregman-Amitai | G06T 7/0012 382/131 |
| 2018/0144465 | A1* | 5/2018 | Hsieh | G06N 3/08 |

OTHER PUBLICATIONS

Suo, Qiuling, et al. "A multi-task framework for monitoring health conditions via attention-based recurrent neural networks." AMIA annual symposium proceedings. vol. 2017. American Medical Informatics Association, 2017. (Year: 2017).*

Lee, Changhee, Jinsung Yoon, and Mihaela Van Der Schaar. "Dynamic-deephit: A deep learning approach for dynamic survival analysis with competing risks based on longitudinal data." IEEE Transactions on Biomedical Engineering 67.1 (2019): 122-133. (Year: 2019).*

Kim, D. H., and T. MacKinnon. "Artificial intelligence in fracture detection: transfer learning from deep convolutional neural networks." Clinical radiology 73.5 (2018): 439-445. (Year: 2018).*

Lee, C. et al., "DeepHit: A Deep Learning Approach to Survival Analysis with Competing Risks," The Thirty-Second AAAI Conference on Artificial Intelligence (AAAI-18), 2018, pp. 2314-2321.

Lee, C. et al., "Dynamic-DeepHit: A Deep Learning Approach for Dynamic Survival Analysis with Competing Risks based on Longitudinal Data," IEEE Transactions on Biomedical Engineering, Feb. 2019, pp. 1-12.

Badgeley, M.A. et al., "Deep learning predicts hip fracture using confounding patient and healthcare variables," Nature, Apr. 30, 2019, pp. 1-10.

Kim, D.H. et al., "Artificial intelligence in fracture detection: transfer learning from deep convolutional neural networks," Clinical Radiology, vol. 73, Iss. 5, Dec. 18, 2017, pp. 439-445.

PCT International Search Report and Written Opinion, PCT Application No. PCT/IB2020/056716, dated Oct. 15, 2020, 11 pages.

India Intellectual Property Office, Indian Patent Application No. 202147060814, dated Sep. 13, 2022, 7 pages.

Schott, A. M. et al. "Ultrasound Discriminates Patients with Hip Fracture Equally Well as Dual Energy X-Ray Absorptiometry and Independently of Bone Mineral Density," *Journal of Bone and Mineral Research*, vol. 10, No. 2, Feb. 1995, pp. 243-249.

Walters, J.R. et al. "Detection of Low Bone Mineral Density by Dual Energy X Ray Absorptiometry in Unsuspected Suboptimally Treated Coeliac Disease," *Gut*, vol. 37, No. 4, Aug. 1995, pp. 220-224.

Areeckal, A.S. et al. "Early Diagnosis of Osteoporosis Using Radiogrammetry and Texture Analysis from Hand and Wrist Radiographs in Indian Population," *Osteoporosis International*, vol. 29, Mar. 2018, pp. 665-673.

Areeckal, A.S. et al. "Current and Emerging Diagnostic Imaging-Based Techniques for Assessment of Osteoporosis and Fracture Risk," *IEEE Reviews in Biomedical Engineering*, vol. 12, Jul. 3, 2018, pp. 254-268.

European Patent Office, Extended European Search Report and Written Opinion, European Patent Application No. 20839666.3, dated Jun. 1, 2023, 5 pages.

* cited by examiner

SYSTEMS AND METHODS FOR APPROXIMATING BONE MINERAL DENSITY AND FRACTURE RISK USING SINGLE ENERGY X-RAYS

BACKGROUND

This invention relates generally to medical imaging, and more particularly to machine learned models for analyzing medical images to characterize patient bone.

Osteoporosis is a widespread disease characterized by the loss of bone mineral density (BMD). Osteoporotic patients are at risk of devastating fractures that result in significant morbidity and mortality. At least 1 in 3 women and 1 in 5 men suffer from an osteoporotic fracture in their lifetime. The current clinically accepted gold-standard to measure BMD is dual energy x-ray absorptiometry (DEXA) which relies on obtaining x-rays of a patient's lumbar spine, hip or forearm at two distinct x-ray energies to calculate the absorption of energy from bone and infer its density. BMD is typically reported as g/cm 2 and is corrected to gender-matched t-scores (when age >50) to arrive at a diagnosis of normal bone mass (>−1 S.D.), low-bone mass (between −1.0 and −2.5 S.D.) or osteoporosis (<−2.5 S.D.) and age-matched z-scores (when age <50) to arrive at a diagnosis of within expected range (>−2.0 S.D.) or below expected range (<=−2.0 S.D.). The t-score or z-score is used in a variety of clinically validated fracture risk models such as CAROC 2010 or Fracture Risk Assessment Tool (FRAX) which may also take into consideration other risk factors such as history of fracture, cigarette, alcohol and glucocorticoid use and the presence of rheumatoid arthritis to estimate the patient's 10 year fracture risk. This fracture risk is used to guide clinical therapy.

While DEXA scans are currently considered a gold-standard for BMD measurement, they require specific equipment and training to perform as well as knowledge to report. These factors result in a more expensive and less ubiquitous test thus limiting the population that can be screened.

In addition to the physical constraints inhibiting the effective use of single-energy x-ray scans to approximate bone mineral density, there are additional difficulties in modeling fracture risk generally that gives fracture risk prediction, particularly in longitudinal osteoporosis studies, many unique challenges. First, time-varying covariates are subject to persistent change throughout the course of a study. This poses a challenge for traditional statistical approaches to survival analysis, which despite being able to model the time-varying covariate setting, often have undesirable or inconsistent statistical properties when making predictions. Additionally, there are often complex dependencies between covariates—some covariates may causally impact covariates measured at a future time point, complicating the analysis, and increasing the risk of drawing incorrect conclusions. Patients may also suffer fractures recurrently, each fracture causing the future likelihood of a fracture to change drastically. Furthermore, recurring fractures causally impact patients' treatment conditions, for example via newly prescribed medication after a first fracture, the effects of which can introduce seemingly paradoxical effects, known as reverse causation, if not accounted for correctly. Finally, many competing risks in addition to fracture, complicate analysis.

SUMMARY

A fracture risk analysis system may train and use one or more statistical models to approximate BMD, t or z-score and/or fracture risk utilizing single energy x-rays. The x-ray may be of any relevant body part, such as the chest, thoracic spine, lumbar spine, pelvis, hip, total body, arm, leg, hand or foot. The fracture risk analysis system may train one or more statistical models (e.g., neural networks) to approximate BMD, t or z-score and/or fracture risk. In one embodiment, a BMD prediction model receives one or more single energy x-ray images and optionally, additional characteristics of a patient's mass or body mass index and x-ray technical parameters describing capture characteristics of the imaging process (including but not limited to manufacturer, source-to-detector distance, mAs, KVP, field of view) to approximate BMD (g/cm2). In one embodiment, a statistical classifier may receive additional characteristics of the patient, such as patient age and sex to approximate t-score or z-score according to accepted population reference standards (i.e., NHANES). In another embodiment, a fracture risk prediction model receives one or more additional characteristics of the patient, such as risk factors, in either binary or continuous formats, including but not limited to: history of previous fracture, smoking history, alcohol or glucocorticoid use (including dose, frequency and length), medication history, or the presence of other comorbidities to predict likelihood of fracture over a period of time (i.e. 3, 5 or 10 years).

One embodiment of the BMD prediction model applies modern machine learning techniques to train a convolutional neural network using a dataset of concurrently performed single energy x-ray and DEXA examinations of the same body part (i.e. lumbar spine). The BMD prediction model receives the single energy x-ray including pixel information along with the technical parameters of the imaging process and is optimized during training to reduce the mean absolute error between the predicted BMD and BMD obtained from the DEXA.

In one embodiment, the fracture risk model receives one or more single energy x-ray images along with a set of patient characteristics at one or more points in time. The characteristics and x-ray for a particular point in time is termed the patient features for the model. The patient features are organized as a time sequence according to the time at which the patient characteristics were determined or an x-ray captured. These may be used to represent a longitudinal characterization of the patient over time. For example, an initial x-ray may be captured of the patient along with a first set of patient characteristics, such as weight, lifestyle, medication, etc. A year later the patient characteristics may be updated, while two years later another x-ray image is captured. The x-ray image data and patient characteristics are thus used as patient features to characterize the patient in the model over time.

The fracture risk model is trained to receive a sequence of patient features (including the x-ray image data and patient characteristics over time) and directly predict future fracture risk for the patient. The fracture risk model may include a recurrent neural network (RNN) that creates a temporal representation that characterizes the patient features. In one embodiment, a RNN node is applied to each sequential set of patient features prior to the final, most recent set of patient features. The hidden states of the RNN are identified and an attention layer generates the temporal representation based on the hidden states for each timestep and the values of the patient features for that timestep. The temporal representation along with the current patient features is input to one or more feed-forward networks to predict the fracture risk for the patient.

The fracture risk may be described as an expected "time to fracture" or may be a predicted probability distribution of a fracture occurring in each sequential year. In some embodiments, in addition to fracture risk, additional events are predicted with an additional feed-forward network connected to the temporal representation, where each feed-forward network is dedicated to an individual type of event that may be predicted, in which case the predictive features before the individual feed-forward networks operates as a shared layer for the different events represented by the feed-forward networks. In various embodiments, the additional event types may predict different events than fracture risk, such as mortality.

The fracture risk model can thus make robust predictions in the time-varying covariate setting (i.e., the changing patient characteristics), an important feature due to the longitudinal nature of osteoporosis studies, which span multiple years, and because a patient's health status and the nature of their medical care may change over time. By using an RNN to model covariates, such as the changing patient characteristics over time, the model covariates can be accounted for at the level of the individual, rather than at an aggregate and patient non-specific level. The RNN has the added benefit of being able to model correlations both between covariates measured at a single time point, and between the covariates at different time points. As a result, the fracture risk model accounts and accommodates for multiple types of irregularities in the data, for example irregularities in longitudinal data collection, or missing covariates (e.g., patient characteristics/data) at a given time point. As a result, because the fracture risk model can use single-energy x-ray images and can be applied to a variable-length patient history, the fracture risk model can be effectively used for individual patients at an initial point in time and effectively account for changing characteristics of that individual patient over time. This approach thus uniquely permits single or temporally sequential single energy x-ray images, optionally in addition to other variables, to directly predict the probability of a patient in sustaining a facture.

The predicted fracture risk is presented to the user to aid in the screening and diagnosis of osteoporosis or to stratify a patient's risk of sustaining an osteoporotic fracture over a period of time. In addition, the effect of various treatments may be identified by varying the patient characteristics of the patient in the current patient features or by simulating additional patient features for an additional time and identifying the effect on predicted fracture risk. For example, the patient characteristics describing current medication use may be modified to add or remove a medication. Those modified patient characteristics that provide an improved fracture risk may then be implemented as an intervention or treatment plan for the patient.

This approach thus predicts BMD, t or z scores, or fracture risk for an individual patient from a single energy X-ray without requiring the additional equipment overhead, training, and practitioner knowledge required for other types of fracture risk prediction and evaluation (such as DEXA scans). In addition, the model structure and characterizing the patient for the fracture risk model as a sequence of patient features over time allows the model to account for modifications in the patient's characteristics over time—allowing for both more accurately evaluating risk for a given individual (effectively accounting for prior patient characteristics), and to evaluate the efficacy of particular interventions.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Figure 1:
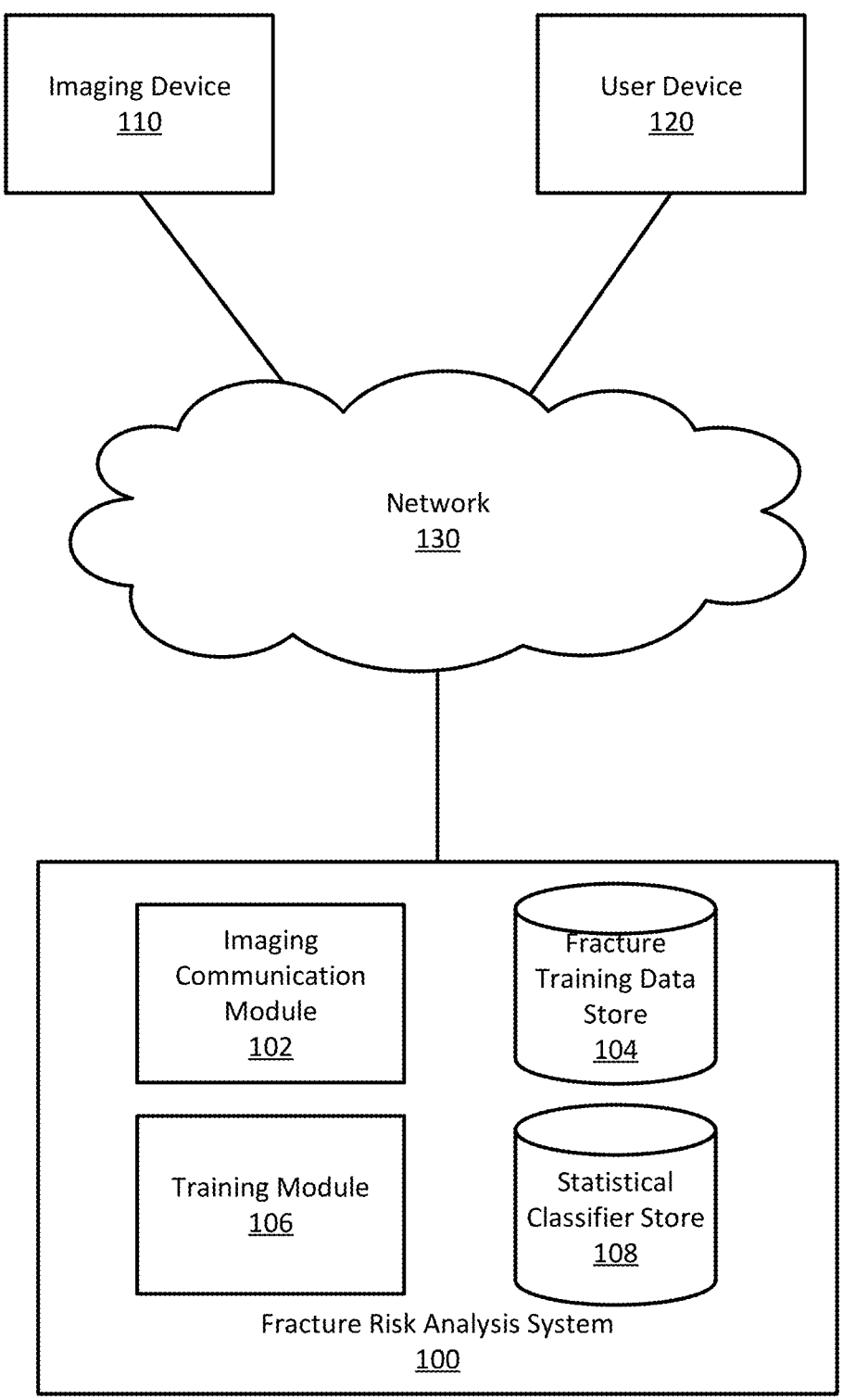
FIG. 1 illustrates an environment for a fracture risk analysis system 100, according to one embodiment.

FIG. 1 illustrates an environment for a fracture risk analysis system 100, according to one embodiment. The fracture risk analysis system 100 trains and applies statistical classifiers to characterize x-ray images obtained by an imaging device 110. In particular, the fracture risk analysis system 100 applies the statistical classifiers to evaluate bone mineral density (BMD), t or z-score, and/or fracture risk based on the single energy x-ray images. An imaging device 110 captures single energy x-ray image patients, which may be analyzed by the fracture risk analysis system 100. The fracture risk analysis system 100 may also analyze x-ray images stored from a repository or from another patient data source. A user device 120 may communicate with the fracture risk analysis system 100 to initiate the fracture risk analysis, provide patient data, and receive and display fracture risk information to users. These computing systems are connected by a network 130 which provides a communication pathway between them. Each of these systems, the imaging device 110, user device 120, and fracture risk analysis system 100 are computing devices and as such may include, among other components, a processor, memory, and wired and/or wireless communication receivers. The computing devices execute the processes as discussed herein via respective processors, which execute instructions stored on respective non-transitory computer-readable mediums as more fully discussed below.

The imaging device 110 captures a single energy x-ray scan of a patient by x-ray capture equipment, such as through traditional or digital radiography. The imaging device 110 captures the x-ray image by emitting radiation towards a subject and capturing the received radiation on a capture system, such as a traditional film or digitally via a detector. The x-ray is termed "single energy" because the x-ray capture equipment uses a single energy level of emitted x-rays to capture the image. Radiography systems may capture the image along with additional information, such as patient information and other characteristics in a related file format, such as the DICOM format (Digital Imaging and Communications in Medicine) that may include standards for storing, printing, and transmitting information for medical imaging.

The fracture risk analysis system 100 includes modules and data stores for training and applying statistical classifiers, including an imaging communication module 102, fracture training data store 104, a training module 106, and a statistical classifier store 108. As discussed more fully below, the statistical classifiers may include a bone mineral density (BMD) prediction model and a fracture risk prediction model, which may be stored in the statistical classifier store 108. The BMD prediction model predicts a BMD score, typically in units gram per cm$^2$ (g/cm$^2$) based on the image data of the single energy x-ray, as further discussed in FIG. 2. Though a BMD score is typically obtained directly via a DEXA scan that uses multiple x-ray energy levels in capturing the image, the BMD prediction model effectively estimates the BMD score based on a single energy level x-ray. The fracture risk prediction model likewise predicts a fracture risk for a patient given one or more single energy level x-rays and patient characteristics, which may be associated with different times, allowing a prediction from single energy level x-rays that can also account for individual longitudinal information about a particular patient. The fracture risk prediction model is further discussed in FIGS. 3 and 4.

The imaging communication module 102 communicates with the imaging device 110 to receive single x-ray images and with user device 120 to receive patient data for application to one of the statistical classifiers of the statistical classifier store 108. The imaging communication module 102 may also receive patient data from a patient records management system or other healthcare management solution. The imaging communication module may also structure the received x-ray images and patient data to generate features used with the desired statistical classifier, for example by generating the sequence of patient features as discussed in FIG. 3. The imaging communication module 102 may also receive instructions from the user device 120 to modify user characteristics (e.g., covariabilities) to evaluate the effects of that modification on the statistical model. For example, to modify a medication and determine an expected future effect on a predicted fracture risk.

The fracture training data store 104 includes training data for training the statistical classifiers. The training data may vary based on the particular statistical classifier being trained. For training the BMD classifier, the training data includes a set of training images that include single energy x-ray images and patient characteristics along with associated BMD scores obtained from a DEXA scan. The x-ray images may include technical characteristics describing the imaging system that captured the images. Likewise, the fracture risk prediction model is trained with one or more single energy x-ray images and associated patient information, which is labeled with the actual fracture incidence of the associated patients. For example, whether the patient experienced a fracture and if so how many years after the associated x-ray image. The fracture incidence may also be described as whether a fracture occurred within one year, three years, five years, or ten years of the fracture, etc.

The patient characteristics may be included to characterize additional risk factors for a patient. In addition to these characteristics that may be derived from the image, additional risk factors may also be represented as features, such as a patient's prior fracture history, smoking history, steroid use, alcohol use, rheumatoid arthritis, osteoporosis therapy, non-osteoporosis medication history, age of menarche, and so forth. These characteristics may be obtained from an electronic patient file or from another source associated with the image being evaluated.

In one embodiment, the training data for each model is determined from the Canadian Multicenter Osteoporosis Study, which includes longitudinal data for over nine-thousand individuals over 19 years. In one embodiment, the training data includes patients over the age of 50 and include baseline images of the thoracic and lumbar spine obtained via digital radiography. Participants in this data set were imaged with x-ray at baseline, 5 years, 10 years, and 16 years, and provided patient information annually until year 19. The associated BMD values were captured by DEXA systems and cumulative readings from the L1-L4 vertebrae. The characteristics of these users included demographic and activity information along with medical history that may affect fracture risk. Example types of this patient information includes:
Age
Sex
Height
Weight
History of Previous Fracture
History of previous or current Cigarette smoking
History of previous or current Alcohol use
Country of birth
Highest Education
Level of exercise at work
Race
Family history of rheumatoid arthritis
Family history of osteoporosis
Current medications with doses and frequencies
Medical History:
  Osteoporosis
  Rheumatoid arthritis
  Osteoarthritis
  Thyroid disease
  Liver disease
  Scoliosis
  Eating disorder
  Breast cancer
  Uterine cancer (for females)
  Inflammatory bowel disease
  Kidney stones
  Hypertension
  Heart attack
  Stroke TIA (Transient Ischemic attack)
  Neuromuscular disease: 1=Parkinson's 2=Multiple Sclerosis 3=Other
  Diabetes: 1=Insulin Dependent, 2=Non-Insulin Dependent
    Age at diagnosis
  Kidney disease
  Phlebitis, thrombophlebitis
  Prostate cancer (for males)
  Paget's Disease of Bone
  COPD
If female:
  Age at menarche
  Age at menopause
  # of live births
  # of pregnancies
  Length of period
  History of breastfeeding
    # of cumulative months
  Oral contraception use
  Progesterone Use
  Estrogen Use These various characteristics describing users may be included as features used by the statistical models as discussed below. Likewise, the same information may be provided by a patient along with at least one x-ray image to use one of the models.

The training module 106 trains the statistical models with the training data stored in the fracture training data store 104. The training process initializes and then trains weights within the models to reduce the loss of the model output relative to the labeled value for a training data item. The training process for each model is described in more detail below.

Figure 2:
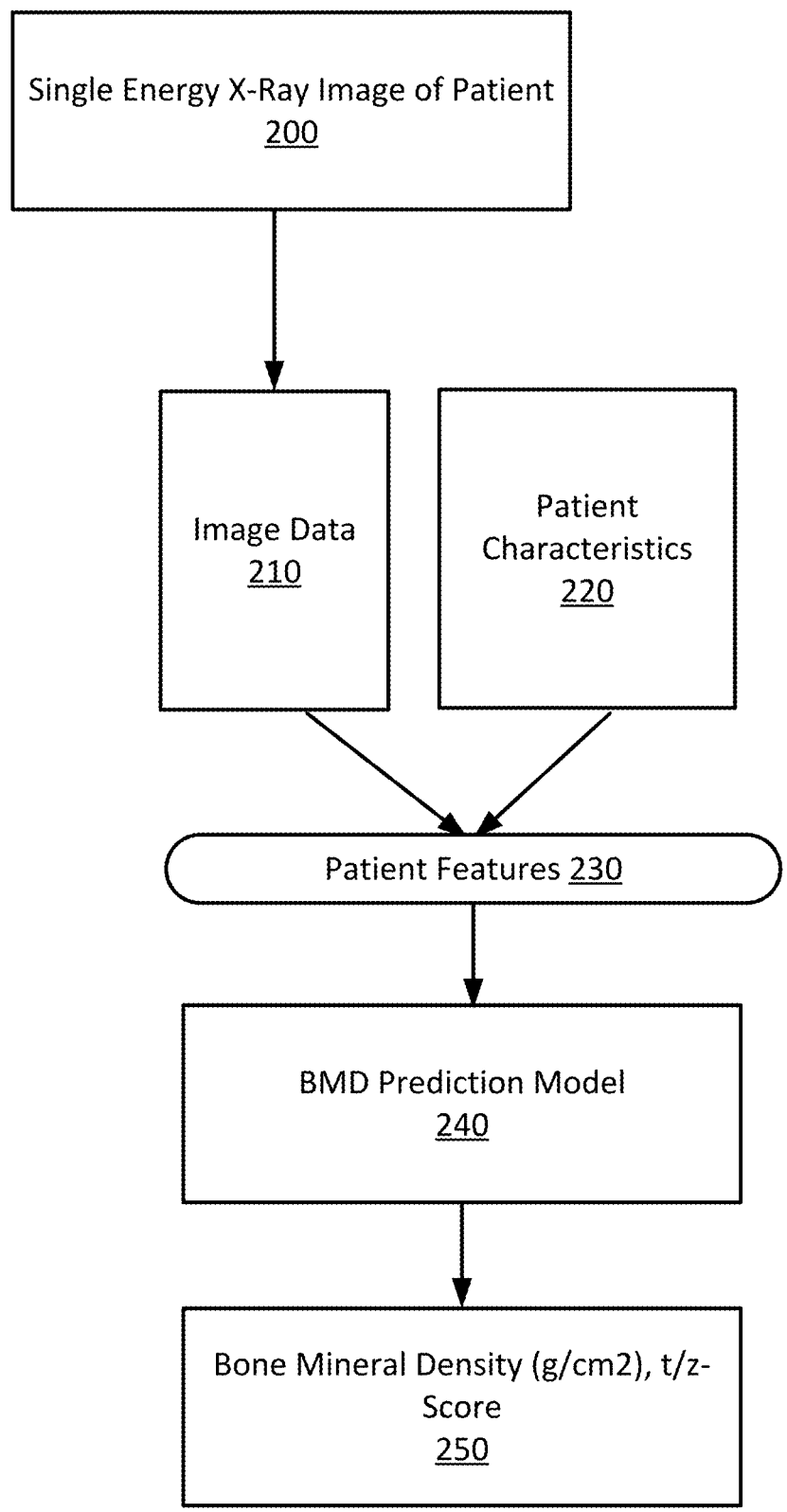
FIG. 2 illustrates an example flow for a BMD prediction model 240 that predicts Bone Mineral Density (BMD), according to one embodiment.

FIG. 2 illustrates an example flow for a BMD prediction model 240 that predicts Bone Mineral Density (BMD), according to one embodiment. To generate an estimated BMD score, features are identified for the BMD prediction model 240, which may broadly include image data 210 and patient characteristics 220. The patient characteristics 220 include various features describing the patient, such as a patient's age, sex, ethnicity, mass, and body mass index (BMI) and other patient information discussed above with respect to the training data and particular risk factors of the patient. The image data 210 includes pixel data of the image and may include technical parameters of the image capture process. The imaging technical parameters may include the power, voltage, exposure, source-to-detector distance, field of view, and manufacturer/model of the device and so forth. The pixel data may include the intensity of each pixel in the image, which may represent the extent to which radiation was absorbed or passed through the body in the captured x-ray image.

A preprocessor may extract image data 210 and patient characteristics 220 from the image file itself, e.g., as embedded in a DICOM image. In other embodiments, the patient characteristics may be retrieved from other sources. In addition to extracting this information, the preprocessor performs a series of quality assurance measures to ensure the information is what is to be expected by the statistical classifier including but not limited to the body part being imaged, the image projection, photometric interpretation and integer bit-depth. The preprocessor produces a probability for the body part and projection of the image. Optionally, the preprocessor segments a region of interest containing the bone structures in the image.

The image data 210 and patient characteristics 220 are combined to create patient features 230. Patient features 230 represent the features to be input to the BMD prediction model 240. The BMD prediction model 240 is a neural network trained to generate a Bone Mineral Density score based on the input patient features 230. The BMD prediction model in some embodiments includes a convolutional neural network (CNN) for processing the image data 210. In various embodiments, the CNN may be a structure such as mobilenet-v2, resnet-50, densenet 121 or inceptionV3. The input size to the CNN may vary in different implementations, and may include, for example, 224×224 or 1024× 1024. The output of the BMD prediction model 240 is a BMD score 250, which may also be evaluated to a t or z-score based on a patient's age and gender.

To train the BMD prediction model 240, a training data set may be obtained with a set of x-rays and associated patient features from the fracture training data store 104. As training labels, the single energy x-ray image may be labeled with a BMD score obtained from a DEXA scan of the same patient, either concurrently with or within a short period of time (i.e., 6 months) from when the single energy x-ray image was obtained. The score from a DEXA scan may be considered the "ground truth" for training the BMD prediction model in one example.

Though shown in FIG. 2 as predicting a BMD score with a BMD prediction model 240, in another embodiment, the architecture shown in FIG. 2 may be used to directly predict a fracture risk based on the patient features 230. In this example, the training data is labeled with actual fracture incidence of patients in the training set for an amount of time after the x-ray image 200 was captured of the patient. This training data, as discussed with respect to training data store 104, may include longitudinal study data of many participants to label the desired output of the risk fracture model with the actual fracture risk over a time period, such as one, five, or ten years from the date of the x-ray. Alternatively, the probability of fracture at any future time can be outputted as a survival curve. These may be used to determine the actual fracture frequency of patients based on the captured x-ray scan.

Accordingly, with the training data, the BMD prediction model 240 may be trained to learn parameters such that an image and other data from a patient may be used to estimate the BMD; similarly the fracture risk model may predict fracture risk based on the learned parameters of the model. Accordingly, one embodiment of the statistical classifier applies machine learning techniques to train a convolutional neural network using a dataset of concurrently performed single energy x-ray and DEXA examinations of the same body part (i.e. lumbar spine). The DEXA examination may be used to determine BMD, and the statistical classifier is trained to predict BMD based on the received single energy x-ray image, which may include pixel information and the technical parameters above. During training, the model may be optimized to reduce the mean absolute error between the predicted BMD (from the model) and the BMD separately obtained from the DEXA scan. Another embodiment of the statistical classifier applies machine learning techniques to train a convolutional neural network using a dataset of concurrently performed single energy x-ray and DEXA examinations of a different body part (i.e. single energy x-ray of thoracic spine and DEXA of lumbar spine). When trained in the same manner, the resulting classifier may be used with a routine chest or thoracic spine x-ray to approximate the BMD of a different body part (i.e., lumbar spine in this example).

Figure 3:
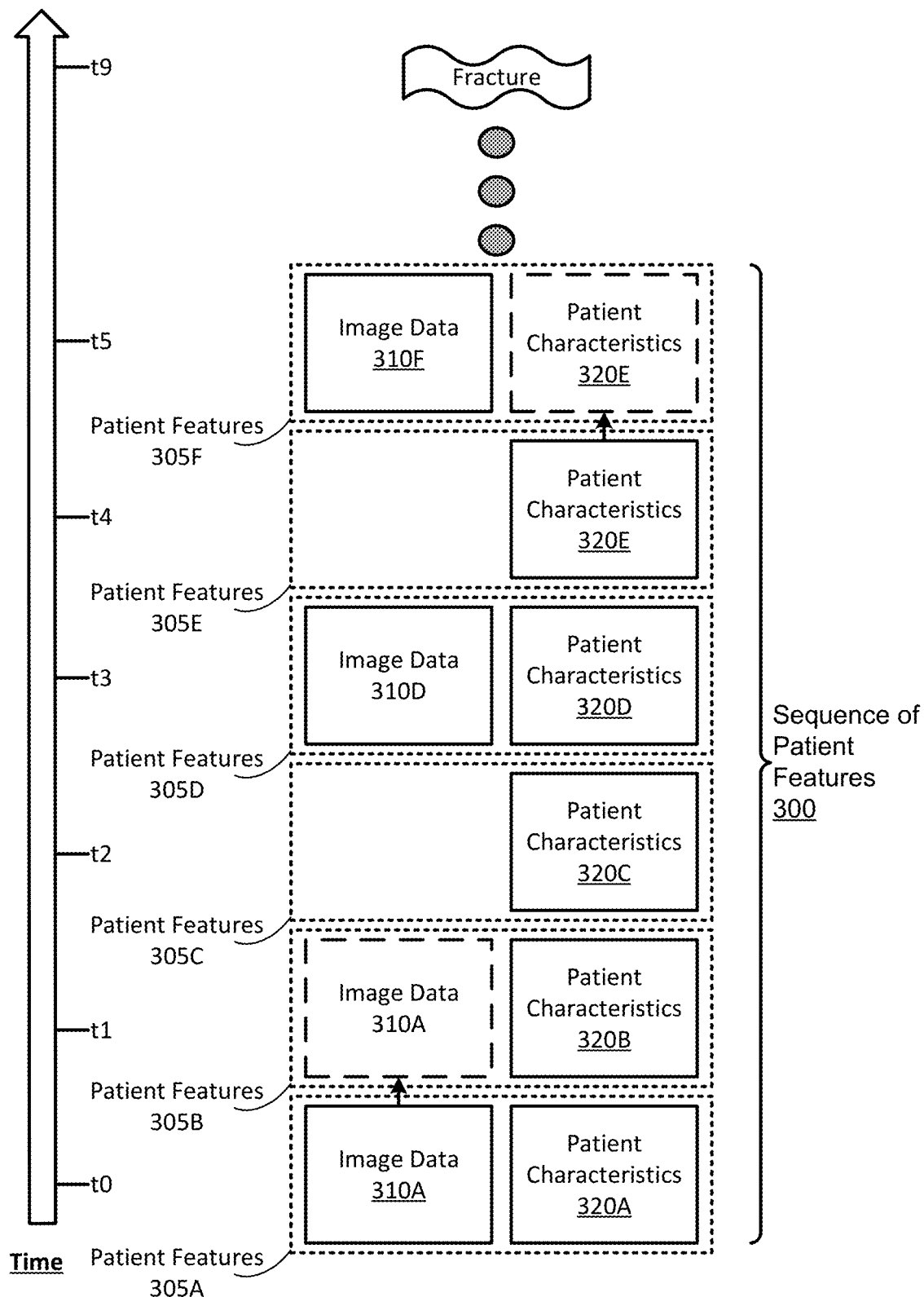
FIG. 3 illustrates an example sequence of patient features for use with an example fracture risk model.

FIG. 3 illustrates an example sequence of patient features for use with an example fracture risk model. To effectively measure fracture risk as a function of time, a fracture risk model may receive as an input a sequence of patient features 300 that represents the patient as x-ray images and patient characteristics vary over time. The sequence of patient features 300 may thus include one or more sets of image data 310 (i.e., single energy x-ray images), along with a set of patient characteristics 320A-F organized according to the time at which the data was obtained from the patient. At each time step, a user may be characterized by a particular combination of image data 310 and patient characteristics 320, which together form a set of patient features for that time step. As discussed above with respect to the training data, the patient characteristics may include patient demographic information, patient medical history, patient drug history, etc, and training data may be obtained based on longitudinal studies of patients over time. Certain patient features may be static (e.g., gender), while others may change (e.g., image data, drug history). To represent the dynamic features as they change over time, the dynamic features are updated as additional information is captured at different points in time. Thus, at time t0 in this example, image data 310A and patient characteristics 320A together form the patient features to represent the patient at time t0. Similarly, at time t3, the image data 310D and patient characteristics 320D form the patient features to represent the patient at time t3.

Though shown as having periodic timesteps in FIG. 3, in practice the associated time with each measurement (e.g., captured image data) may vary; the time difference (or delta) between two reported modifications of the patient characteristics may in practice be 10 months in one instance and 15 months in another. The data for each type of data may be updated asynchronously and at different time periods. This may occur, for example, if a patient returned a survey or otherwise indicated a change to the patient's lifestyle of medication history, but did not have a new captured x-ray image. Alternatively, if a user had a new image captured but did not provide new characteristics. For example, at time t1, new patient characteristics are recorded, but no new image data is captured. Similarly, at t5, new image data 310F was captured, but no new patient characteristics were recorded.

In one embodiment, to generate a complete set of patient features for each timestep, when new data is received for type of data, the set of patient features for that timestep is assembled by including the prior values of the other features that were not updated. For example, at time t1, when updated patient characteristics 320B are received (but no new image data 310 was captured), the prior image data, i.e., image data 310A, is used as the image data for time t1 in the patient features for time t1. Similarly, when image data 310F is received at time t5, the previously-captured patient characteristics 320E may be used to assemble a set of dynamic patient features for the time step t5. Though not shown in FIG. 3, the same may occur at time t2 and t4 with image data 310A and image data 310D, respectively.

Figure 4:
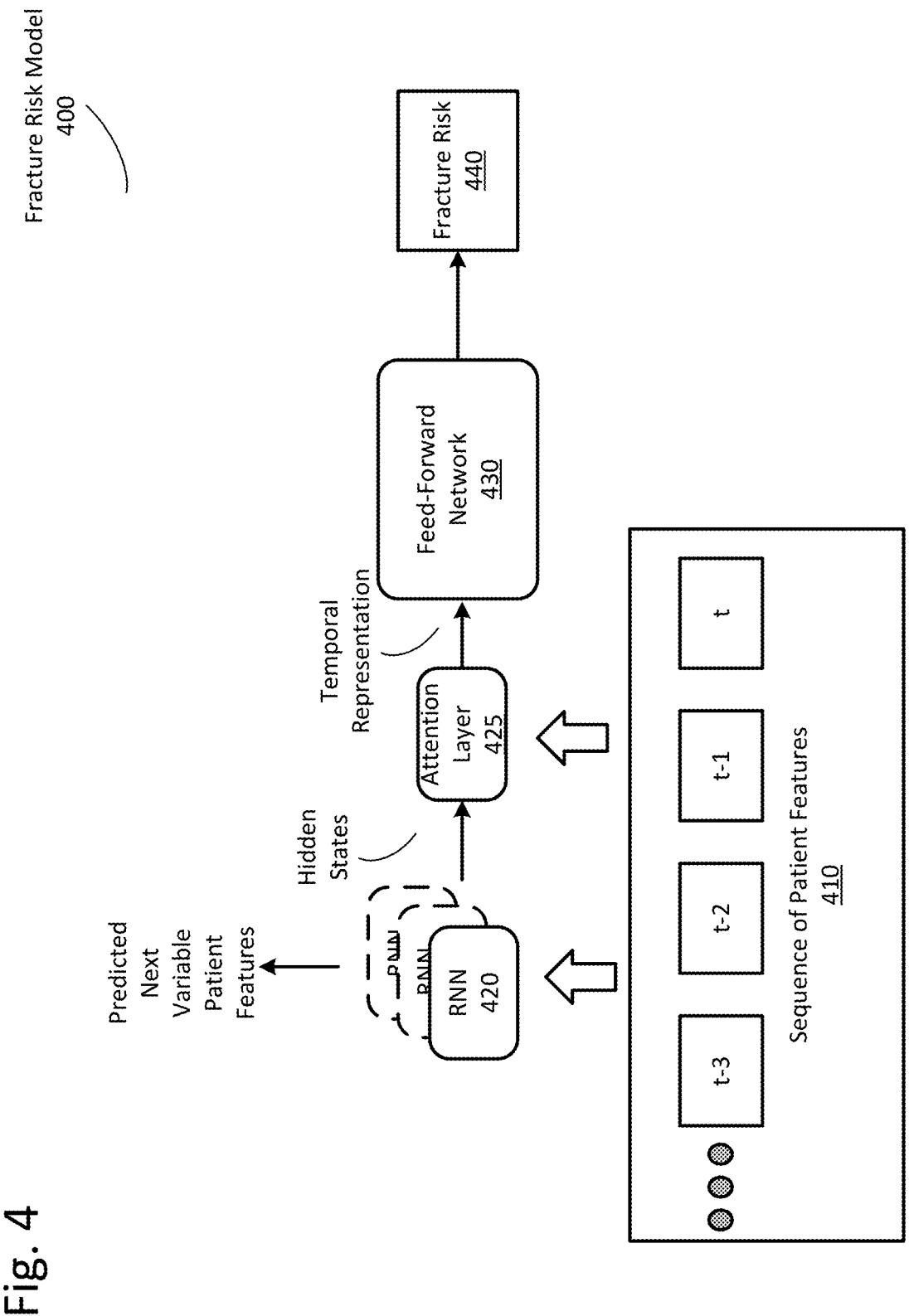
FIG. 4 illustrates an example architecture for a fracture risk model 400.

FIG. 4 illustrates an example architecture for a fracture risk model 400. The fracture risk model receives the sequence of patient features 410 and processes the sequence of patient features 410 to predict a fracture risk 440. The sequence of patient features has at least one time step as discussed with respect to FIG. 3, and includes one or more single energy x-ray images of the patient, along with patient characteristics (i.e., potential covariates and risk factors). Accordingly, as a whole, the sequence of patient features includes a set of at least one x-ray images and patient characteristics organized in time order according to the capture time (of images) or survey response (for patient characteristics).

The fracture risk model 400 may include a convolutional or recurrent neural network (RNN) or combination of statistical models that analyzes the sequence of patient features 410 to evaluate the fracture risk. In the embodiment shown in FIG. 4, the fracture risk model 400 includes a recurrent neural network layer 420 and a feed-forward network 430. The recurrent neural network layer 420 is used to generate a temporal representation of the sequence of patient features and thus characterize the dynamic length of the sequence of patient features 410 to a fixed-length representation for evaluation by the feed-forward network 430.

The recurrent neural network may have various forms, such as Gated Recurrent Unit (GRU), Long Term Short Memory (LTSM), or a bidirectional RNN. In general, each set of patient features, is applied to the RNN layer. The RNN 420 is trained to predict the next variable patient features in the sequence of patient features and in training the RNN may learn weights that improve that prediction. In addition, because the time step for each set of patient features is variable, an additional value may be added that describes the difference in time value from one set of patient features to the next in the sequence. In one embodiment, the patient features are augmented by applying the BMD prediction model, e.g., as discussed with respect to FIG. 2 to the image data to generate a predicted BMD score for the set of patient features.

In one embodiment, the hidden states at each iteration of the RNN are used to generate the temporal representation of the sequence. In this embodiment, an attention layer may be used to combine the information represented in the hidden states with the corresponding set of patient features in the sequence of patient features. In some embodiments, the attention layer may thus effectively weigh the relative value of information embedded at different points in time in the sequence of patient features. In one example embodiment, the RNN layer may include two layers each having a hundred nodes.

In one embodiment (not shown in FIG. 4), the RNN layer 420 is applied to each set of the patient features except the most recent set of patient features. The most recent set of patient features may be concatenated to a temporal representation generated based on the previous patient features in the sequence. This approach allows the feed-forward network access to the temporal representation as well as direct access to the most recent set of patient features.

The temporal representation is then input to the feed-forward network 430 to generate the fracture risk score 440. The feed-forward network comprises a set of feed-forward connected layers, which are fully-connected in some embodiments.

As discussed above, the fracture risk score 440 may be in the form of a probability of fracture within a one, five, or ten year period. Alternatively, the probability of fracture at any future time can be outputted as a survival curve or another probability distribution. In some embodiments, before outputting the fracture risk score 440, the feed-forward network 430 includes a softmax layer.

In additional embodiments, the temporal representation operates as a shared layer that may be used to predict additional events in addition to fracture risk. To do so, additional feed-forward networks may be used for other event types and receive the temporal representation created by the RNN and (if used) the attention layer.

To train the fracture risk model 400, the training module 106 may use the fracture data as a label while jointly training the various layers of the network. In one embodiment, network weights were initialized using Xavier initialization, and ReLU non-linearities were used as activation functions. A dropout factor of 0.6 was used, to help prevent model overfitting.

The fracture risk model 400 may also be used to determine effective treatment for a patient. Because the temporal representation accounts for prior history of a patient in the modeling, the structure of the model permits treatment effects to be evaluated specific to that user's individual history. To simulate a treatment for a patient, when a sequence of patient features is applied to the fracture risk model 400 and a fracture risk is determined, the sequence of patient features may be modified to describe an alternate patient characteristic that simulates the treatment. In one embodiment, an additional time step may be added 6 months after the most recent time step that adds a different exercise level or drug history representing the modified user characteristics of the treatment. In another embodiment, characteristics of the most-recent patient features may be modified in situ to create the modified sequence of patient features. The modified sequence of patient features may be applied to the model to evaluate the difference in resulting predicted fracture risk. Various of such modifications may be performed to evaluate and demonstrate efficacy of interventions to users, and may be used to determine a course of treatment (i.e., to administer a drug which appears effective based on the modified sequence of patient features).

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A computer-implemented method for predicting fracture risk for a patient based on single energy x-ray image data, comprising:
   identifying a chronologically ordered sequence of sets of patient features for a patient, each set of patient features describing measured information about a patient, and at least one of the set of patient features including a single energy x-ray image;
   applying the chronologically ordered sequence of sets of patient features to a recurrent neural network (RNN) to determine a temporal representation;
   applying the temporal representation to a feed-forward network to predict a fracture risk for the patient modifying the chronologically ordered sequence of sets of patient features to simulate a treatment for the patient; and
   applying the modified ordered sequence of sets of patient features to the recurrent neural network and the feed-forward network to determine the predicted fracture risk of the treatment for the patient.

2. The computer-implemented method of claim 1, wherein the sets of patient features include a bone mineral density (BMD) score determined by inputting the single energy x-ray image into a machine-trained BMD model.

3. The computer-implemented method of claim 2 wherein the machine-trained BMD model includes a convolutional neural network applied to the single energy x-ray image.

4. The computer-implemented method of claim 1 wherein the fracture risk is a probability distribution.

5. The computer-implemented method of claim 1, wherein the temporal representation is applied to another feed-forward network that predicts another type of event.

6. The computer-implemented method of claim 5 wherein the feed-forward network is jointly trained with the recurrent neural network and the other feed-forward network that predicts another type of event.

7. A computer-implemented method of predicting bone mineral density, comprising:
   receiving a training set of single energy x-ray images, each associated with a bone-mineral density (BMD) determined from a DEXA scan;
   training a statistical model to predict a BMD based on the BMD associated with the training single energy x-ray images;
   receiving a single energy x-ray image of a patient, wherein the single energy x-ray images are images of a first body part and the associated bone-mineral density is determined from a DEXA scan of another body part; and
   determining an estimated BMD score by applying the trained statistical model to the single energy x-ray image of the patient.

8. The computer-implemented method of claim 7, wherein the training set includes patient characteristics associated with the patients of the single energy x-ray images, and the statistical model is trained with the patient characteristics.

9. A non-transitory computer-readable medium for predicting fracture risk for a patient based on single energy x-ray image data, the computer-readable medium including computer-readable program instructions that when executed by a processor cause the processor to:
   identify a chronologically ordered sequence of sets of patient features for a patient, each set of patient features describing measured information about a patient, and at least one of the set of patient features including a single energy x-ray image;
   apply the chronologically ordered sequence of sets of patient features to a recurrent neural network (RNN) to determine a temporal representation;
   apply the temporal representation to a feed-forward network to predict a fracture risk for the patient;
   modifying the chronologically ordered sequence of sets of patient features to simulate a treatment for the patient; and
   applying the modified ordered sequence of sets of patient features to the recurrent neural network and the feed-forward network to determine the predicted fracture risk of the treatment for the patient.

10. The computer-readable medium of claim 9, wherein the sets of patient features include a bone mineral density (BMD) score determined by inputting the single energy x-ray image into a machine-trained BMD model.

11. The computer-readable medium of claim 10 wherein the machine-trained BMD model includes a convolutional neural network applied to the single energy x-ray image.

12. The computer-readable medium of claim 9 wherein the fracture risk is a probability distribution.

13. The computer-readable medium of claim 9, wherein the temporal representation is applied to another feed-forward network that predicts another type of event.

14. The computer-readable medium of claim 13 wherein the feed-forward network is jointly trained with the recurrent neural network and the other feed-forward network that predicts another type of event.

15. A non-transitory computer-readable medium of predicting bone mineral density, the computer-readable medium including computer-readable program instructions that when executed by a processor cause the processor to:

receive a training set of single energy x-ray images, each associated with a bone-mineral density (BMD) determined from a DEXA scan and a set of patient characteristics;

train a statistical model to predict a BMD based on the BMD associated with the training single energy x-ray images;

receive a single energy x-ray image of a patient, wherein the single energy x-ray images are images of a first body part and the associated bone-mineral density is determined from a DEXA scan of another body part; and determine an estimated BMD score by applying the trained statistical model to the single energy x-ray image of the patient.

16. The computer-readable medium of claim 15, wherein the training set includes patient characteristics associated with the patients of the single energy x-ray images, and the statistical model is trained with the patient characteristics.

* * * * *